(12) United States Patent
Karicherla et al.

(10) Patent No.: US 7,627,366 B1
(45) Date of Patent: Dec. 1, 2009

(54) ANALYSIS OF POLARIZATION INFORMATION

(75) Inventors: Annapurna Karicherla, Valencia, CA (US); Xiaoyi Min, Thousand Oaks, CA (US); Xiaozheng Zhang, Valencia, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 304 days.

(21) Appl. No.: 11/123,300

(22) Filed: May 6, 2005

Related U.S. Application Data

(60) Provisional application No. 60/572,016, filed on May 17, 2004.

(51) Int. Cl.
*A61N 1/37* (2006.01)

(52) U.S. Cl. .................................. 600/510; 607/27

(58) Field of Classification Search ............. 607/26–28; 600/510
See application file for complete search history.

(56) References Cited

U.S. PATENT DOCUMENTS

| | | | | |
|---|---|---|---|---|
| 4,121,576 A | * | 10/1978 | Greensite .................... 600/512 |
| 4,674,518 A | | 6/1987 | Salo .......................... 128/695 |
| 4,712,555 A | | 12/1987 | Thornander et al. ... 128/419 PG |
| 4,766,901 A | | 8/1988 | Callaghan ............. 128/419 PG |
| 4,773,401 A | | 9/1988 | Citak et al. ............ 128/419 PG |
| 4,788,980 A | | 12/1988 | Mann et al. ............ 128/419 PG |
| 4,905,705 A | | 3/1990 | Kizakevich et al. |
| 4,940,052 A | | 7/1990 | Mann et al. ............ 128/419 PG |
| 4,944,298 A | | 7/1990 | Sholder ................. 128/419 PG |
| 4,951,682 A | | 8/1990 | Petre |
| 5,003,976 A | | 4/1991 | Alt ........................ 128/419 PG |
| 5,058,583 A | | 10/1991 | Geddes et al. .......... 128/419 D |
| 5,154,171 A | | 10/1992 | Chirife |
| 5,184,615 A | * | 2/1993 | Nappholz et al. ............. 607/14 |
| 5,271,393 A | * | 12/1993 | Callaghan ..................... 607/14 |
| 5,391,190 A | | 2/1995 | Pederson et al. .............. 607/23 |
| 5,431,693 A | * | 7/1995 | Schroeppel ................... 607/28 |
| 5,466,254 A | | 11/1995 | Helland ....................... 607/123 |
| 5,476,483 A | | 12/1995 | Bornzin et al. ................ 607/17 |
| 5,531,772 A | | 7/1996 | Prutchi ........................ 607/17 |
| 5,643,327 A | | 7/1997 | Dawson et al. ................ 607/24 |
| 5,741,311 A | * | 4/1998 | McVenes et al. ............. 607/28 |
| 5,800,467 A | | 9/1998 | Park et al. |
| 5,974,340 A | | 10/1999 | Kadhiresan |

(Continued)

FOREIGN PATENT DOCUMENTS

EP 1 118 307 A1 * 7/2001

(Continued)

OTHER PUBLICATIONS

Ezekowitz, Justin A. et al., "Anemia Is Common in Heart Failure and Is Associated With Poor Outcomes," *Circulation*, 2003; vol. 107, pp. 223-225.

(Continued)

*Primary Examiner*—Carl H Layno
*Assistant Examiner*—Jessica Reidel

(57) ABSTRACT

An exemplary method includes providing a first value indicative of electrode polarization, delivering a cardiac stimulus and determining a second value indicative of electrode polarization associated with the cardiac stimulus, comparing the second value to the first value to determine whether a change in cardiac condition has occurred and, based at least in part on the comparing, deciding whether to adjust a cardiac stimulation therapy.

8 Claims, 10 Drawing Sheets

U.S. PATENT DOCUMENTS

| | | |
|---|---|---|
| 6,188,927 B1 | 2/2001 | Lu et al. |
| 6,278,894 B1 | 8/2001 | Salo et al. .................. 600/547 |
| 6,314,323 B1 | 11/2001 | Ekwall ........................ 607/23 |
| 6,445,951 B1 | 9/2002 | Mouchawar |
| 6,456,880 B1 | 9/2002 | Park et al. |
| 6,459,929 B1 | 10/2002 | Hopper et al. ............. 600/513 |
| 6,473,647 B1 * | 10/2002 | Bradley ....................... 607/27 |
| 6,473,649 B1 | 10/2002 | Gryzwa et al. .............. 607/28 |
| 6,522,914 B1 | 2/2003 | Huvelle et al. ............. 600/509 |
| 6,522,924 B1 | 2/2003 | Meier ........................ 607/28 |
| 6,539,261 B2 | 3/2003 | Dal Molin .................. 607/20 |
| 6,711,439 B1 * | 3/2004 | Bradley et al. ................ 607/9 |
| 6,725,091 B2 | 4/2004 | Dal Molin .................... 607/2 |
| 6,748,261 B1 * | 6/2004 | Kroll et al. ................. 600/510 |
| 6,751,503 B1 | 6/2004 | Kroll |
| 6,810,284 B1 * | 10/2004 | Bradley ...................... 600/510 |
| 2002/0002389 A1 | 1/2002 | Bradley et al. |
| 2002/0161310 A1 | 10/2002 | Daum |
| 2003/0014084 A1 * | 1/2003 | VanHout ....................... 607/9 |
| 2003/0083708 A1 * | 5/2003 | Bradley et al. ............... 607/27 |
| 2003/0153957 A1 | 8/2003 | Bradley ...................... 607/27 |
| 2003/0195580 A1 * | 10/2003 | Bradley et al. .............. 607/28 |
| 2003/0199955 A1 | 10/2003 | Struble et al. |
| 2004/0127944 A1 | 7/2004 | Casset |
| 2004/0220635 A1 * | 11/2004 | Burnes ....................... 607/17 |
| 2004/0267142 A1 | 12/2004 | Paul |

FOREIGN PATENT DOCUMENTS

| | | | |
|---|---|---|---|
| WO | WO 01/10498 A1 * | 2/2001 | |
| WO | WO 01/45792 | 6/2001 | |

OTHER PUBLICATIONS

Androne, Ana-Silvia, MD et al., "Hemodilution Is Common in Patients With Advanced Heart Failure," *Circulation*, 2003;vol. 107, pp. 226-229.

Freedman, Roger A., MD et al., "*Correlation between Magnitude of Lead Polarization and Ejection Fraction in Pacemaker Patients*," (Abstract).

Shamsham, Fadi, M.D. et al., "Essentials of the Diagnosis of Heart Failure," *Am. Fam Physician*, 2000;vol. 61, No. 5, pp. 1319-1328.

Tanner, Hildegard et al., "The Prevalence of Anemia in Chronic Heart Failure," *Internal J of Cardiology*, 2002;vol. 86, pp. 115-121.

Stambler, Bruce S. et al., "*Serial Changes in Right Ventricular Apical Pacing Lead Impedance Predict Changes in Left Ventricular Ejection Fraction and Functional Class in Heart Failure Patients*," PACE 2005; 28:S50-S53.

de Cock Carel C. et al., "*Hemodynamic Benefits of Right Ventricular Outflow Tract Pacing: Comparison with Right Ventricular Apex Pacing*," PACE 1998; 21:536-541.

NonFinal Office Action, mailed Oct. 11, 2007: Parent U.S. Appl. No. 11/231,734.

Final Office Action, mailed May 13, 2008: Related U.S. Appl. No. 11/231,734.

US 6,434,427, 08/2002, Meier (withdrawn)

\* cited by examiner

ANALYSIS OF POLARIZATION INFORMATION

RELATED APPLICATION

This application claims the benefit of U.S. Provisional Application Ser. No. 60/572,016, filed May 17, 2004, entitled "Analysis of Polarization Information," which is incorporated by reference herein.

TECHNICAL FIELD

Subject matter presented herein relates generally to cardiac pacing and/or stimulation therapy. Various examples concern mechanisms for monitoring heart failure.

BACKGROUND

Adequate treatment and prognosis of heart failure patients generally relies on periodic monitoring of characteristics indicative of heart failure. Such characteristics may include cardiac pressure, cardiac volume, ejection fraction and blood flow. In turn, the characteristics may help a care provider to classify a patient's condition, for example, according to the four class scheme of the New York Heart Association (NYHA): Class I—patients with no limitation of activities; they suffer no symptoms from ordinary activities; Class II—patients with slight, mild limitation of activity; they are comfortable with rest or with mild exertion; Class III—patients with marked limitation of activity; they are comfortable only at rest; and Class IV—patients who should be at complete rest, confined to bed or chair; any physical activity brings on discomfort and symptoms occur at rest. Proper treatment of heart failure often relies on assessment of a patient's classification, see, e.g., Shamsham and Mitchell, "Essentials of the diagnosis of heart failure," Am. Fam. Phys., Mar. 1, 2000 (pp. 1319-1330). For example, Shamsham and Mitchell present an algorithm for diastolic dysfunction and systolic dysfunction that references the NYHA classes.

In general, heart failure can perhaps be arrested, even temporarily remitted, but never cured due to the nature of its most common causes (coronary artery disease leading to myocardial infarction leading to permanently destroyed or damaged myocardial substrate). Therefore, a patient with heart failure requires careful and attentive care and disease management, particularly as the disease state progresses. Once fitted with an implantable pacemaker or intercardiac defibrillator device (ICD), patient monitoring becomes more important and typically more frequent.

Cardiac pressure measurement and echocardiograph techniques can reliably monitor heart failure. However, both techniques require specialized equipment. In vivo measurement of cardiac pressure typically requires use of a catheter lead with a pressure sensitive sensor and echocardiograph techniques cannot be achieved in vivo and rely on external equipment. Indeed, echocardiograph equipment usually requires an in-office consultation. An increase in frequency of monitoring can thus have a tremendous impact on a patient's quality of life. While cardiac pressure measurement may not require in-office consultation, it may require a patient to undergo surgical procedure to implant specialized equipment.

A need exists for techniques for monitoring characteristics of heart failure that have a lesser impact on the patient and her lifestyle. In particular, a need exists for techniques that can be implemented through use of existing, implanted equipment. Various exemplary mechanisms described herein aim to satisfy these and/or other needs.

SUMMARY

An exemplary method includes providing a first value indicative of electrode polarization, delivering a cardiac stimulus and determining a second value indicative of electrode polarization associated with the cardiac stimulus, comparing the second value to the first value to determine whether a change in cardiac condition has occurred and, based at least in part on the comparing, deciding whether to adjust a cardiac stimulation therapy. Various other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like are typically numerals or reference designators will be used to reference like parts or elements throughout.

Exemplary Stimulation Device

The techniques described below are intended to be implemented in connection with any stimulation device that is configured or configurable to delivery cardiac therapy and/or sense information germane to cardiac therapy.

Figure 1:
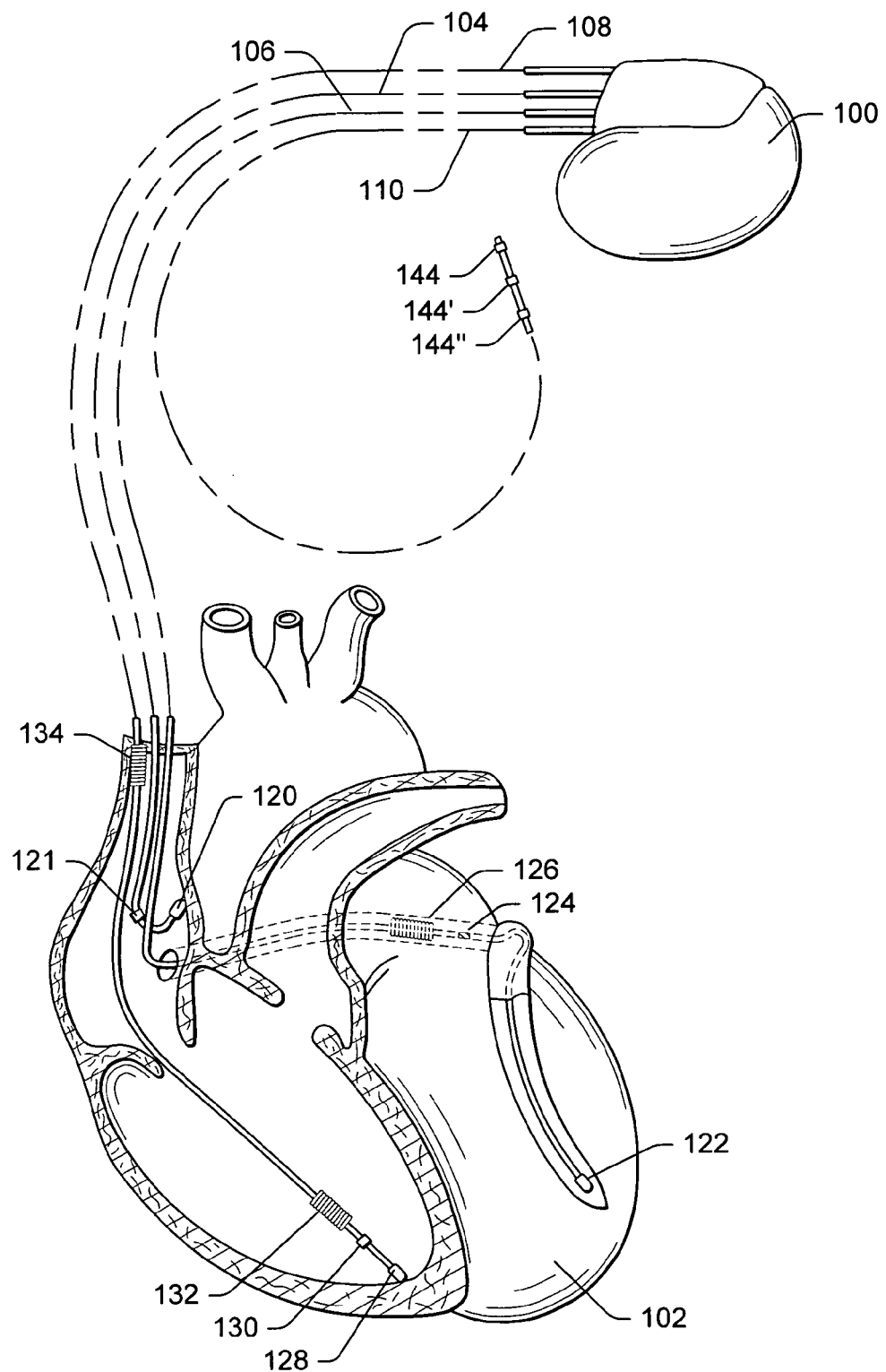
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of nerves or other tissue. Such a lead may include bifurcations or legs. For example, an exemplary coronary sinus lead includes pacing electrodes capable of delivering pacing pulses to a patient's left ventricle and at least one electrode capable of stimulating an autonomic nerve.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava.

Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead.

Figure 2:
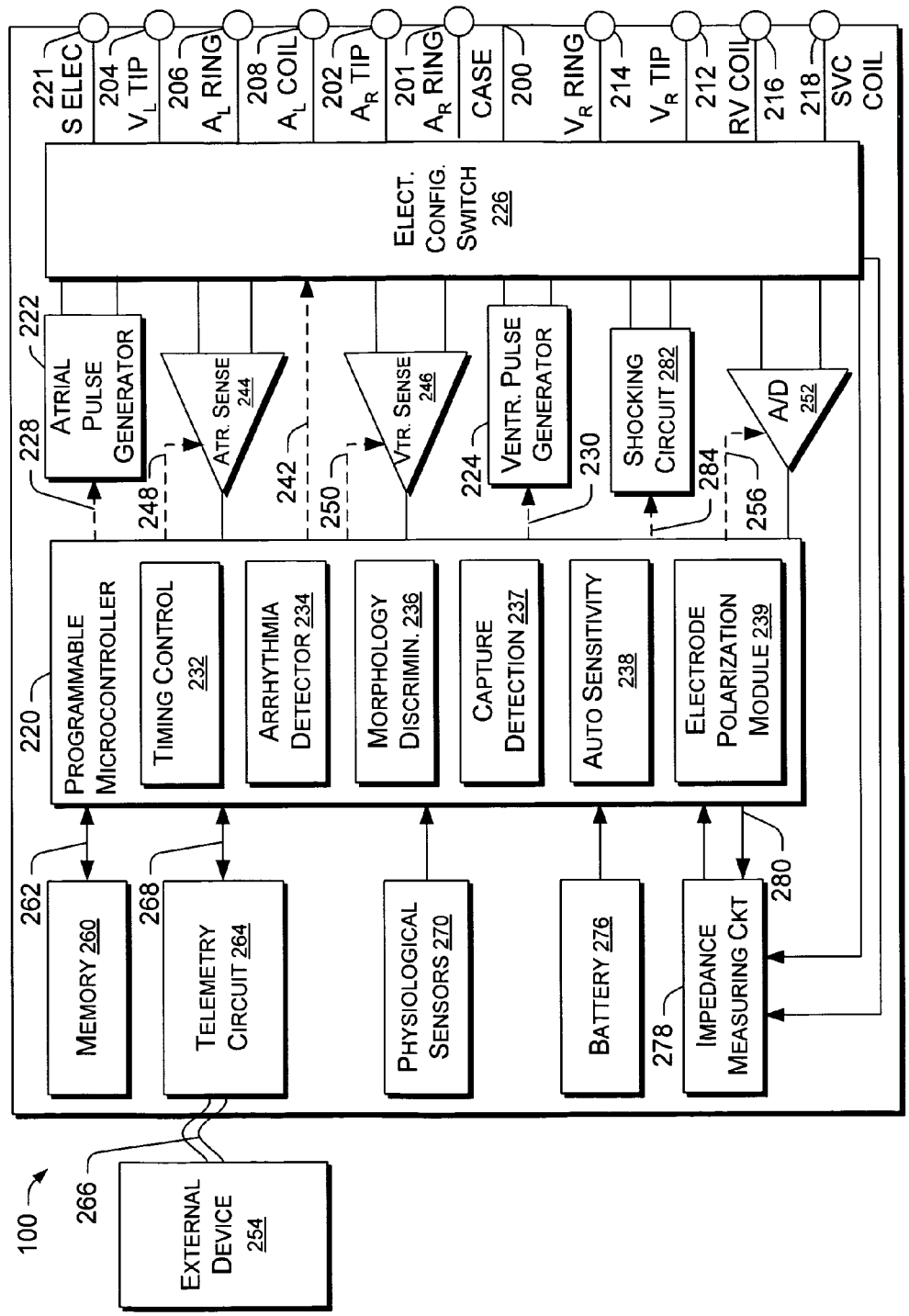
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237, an auto sensing module 238 and an electrode polarization module 239. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The electrode polarization module 239, as described herein, may aid in acquisition, analysis, etc., of information relating to electrode potentials (e.g., after potentials, polarization artifacts, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves" or "Fib-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention. Such a module is optionally suitable for performing various exemplary methods described herein. For example, such a module (e.g., the module 234, the module 239, etc.) optionally allows for analyses related to action potentials (e.g., MAPs, T waves, etc.) and characteristics thereof (e.g., alternans, activation times, repolarization times, derivatives, etc.).

Cardiac signals are also applied to inputs of an analog-to-digital (A/D) data acquisition system 252. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used. Impedance measurements for unipolar (electrode to case electrode), bipolar or multipolar electrode configurations may be possible depending on features (e.g., number of leads, switching, number of electrodes, etc). Impedance may be intracardiac, intrathoracic or other.

As already mentioned, the impedance measuring circuit 278 may be used to acquire impedance information. As described below, such impedance information may be used in conjunction with information related to electrode potentials. For example, various exemplary devices, methods or systems may use the circuit 278 and the electrode polarization module 239 to acquire information, analyze information and determine suitable therapy or cardiac condition. The exemplary circuit 278 and the exemplary polarization module 239 may acquire information for a particular beat (i.e., a cardiac cycle), for different beats, on a beat-by-beat basis or other basis.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3A:
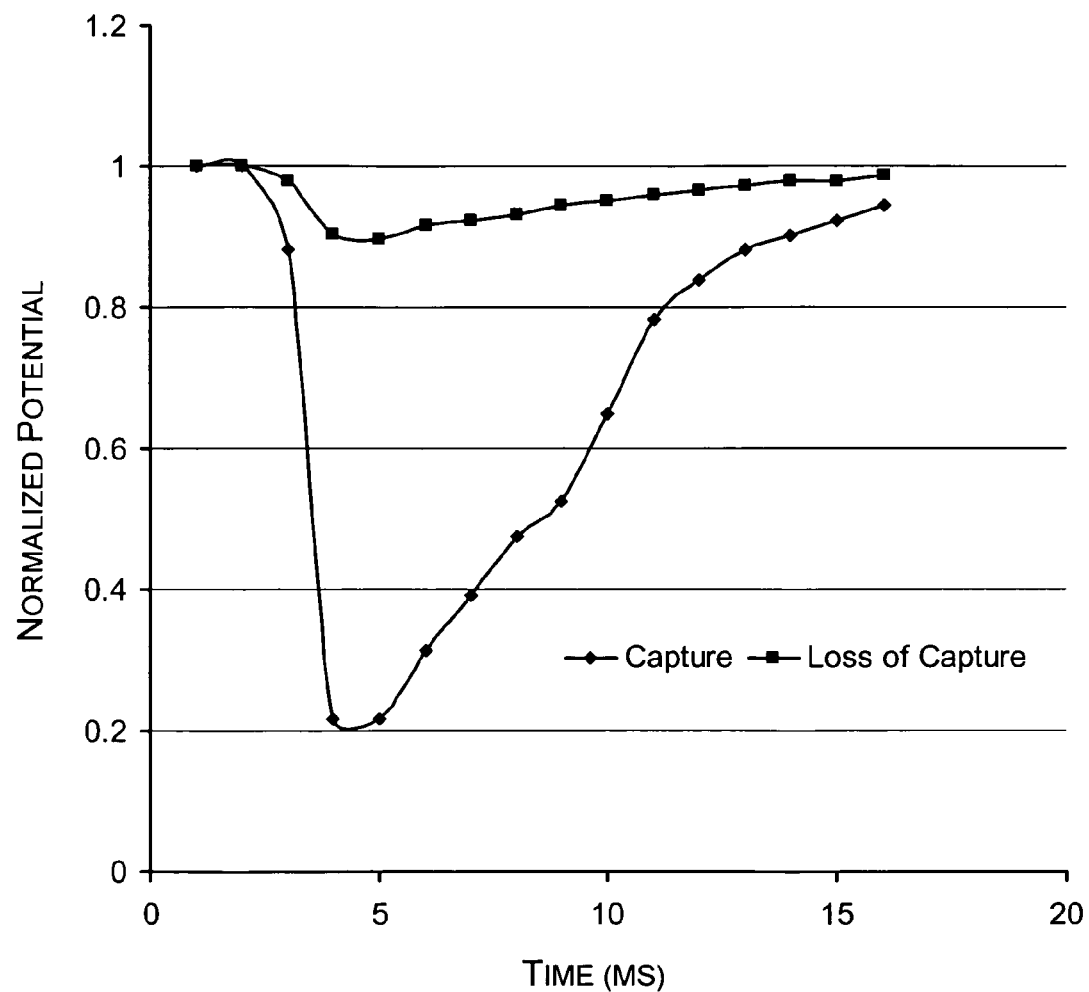
FIG. 3A is a plot of normalized potential versus time for a capture event and a loss of capture event.

FIG. 3A shows an exemplary plot 300 of normalized potential versus time for a stimulus that resulted in an evoked response (diamond markers) and for a stimulus that did not result in an evoked response (square markers). A stimulus that results in an evoked response is classified "capture" while a stimulus that does not result in an evoked response is classified as "non-capture". When non-capture follows capture, then the response may be classified as loss of capture. Such plots of potential versus time, when acquired by an implanted device, are typically referred to as intracardiac electrograms or IEGMs. Some conventional implantable cardiac therapy devices are capable of acquiring, analyzing and even storing IEGMs.

The potentials over time for the capture and the non-capture scenarios of the plot 300 include contributions from cardiac activity and other activity. Cardiac activity includes depolarization of cardiac tissue and repolarization of cardiac tissue. Such activity may exist even in absence of "capture" as localized depolarization near an electrode may occur following a sub-threshold stimulus that is insufficient to cause global depolarization, i.e., insufficient to cause capture. Other activity includes artifacts such as electrode polarization, which is present to some degree whenever a potential is applied across two electrodes (e.g., whether unipolar, bipolar, etc.). Thus, the potentials of plot 300 include at least some electrode polarization information and because the potentials are acquired after delivery of a stimulus, the electrode polarization information is typically referred to as electrode "after" potential information.

Electrode polarization depends on a various factors such as pulse duration (e.g., pulse width), pulse energy, electrode type, pulse phase (e.g., monophasic, biphasic or multiphasic), etc. For example, during delivery of a stimulus, polarization resistance typically rises over time as electricity is being conducted through a wire to an electrode (e.g., negatively charged), an electrolytic solution (e.g., fluid, tissue, etc.) and then to a return electrode (e.g., positively charged), which causes positive ions in the electrolytic solution to migrate toward the negatively charged electrode and negative ions migrate toward the positively charged electrode. Immediately or shortly after delivery of the pulse an after potential exists between the electrodes due to the ion imbalance; however, at some point in time this potential begins to dissipate as ions migrate away from the electrodes as to achieve equilibrium in absence of the applied inter-electrode potential. The process of migrating away from the electrodes may be characterized by a time constant, which may depend on ion concentration, fluid flow, mixing, myocardial activity, blood composition, etc. Again, implantable devices typically acquire potential information only after delivery of a stimulus and hence such information includes after potential information.

Referring to the plot 300 and the data for the loss of capture scenario, the deviation in potential from baseline includes after potential that slowly dissipates. The magnitude of non-capture potential data may be around an order less than that of the capture scenario. Further, after potential typically contributes more percentage-wise to amplitude than in the capture scenario. Low polarization electrodes are commonly used to minimize after polarization, which is sometimes referred to as polarization artifact as it may interfere with capture/non-capture determinations. In addition, sensing algorithms may seek to adjust for after potential or polarization artifacts through use of hardware and/or software.

Potential data may also be acquired following a stimulus delivered during a refractory period of the myocardium wherein even a suprathreshold stimulus voltage or energy will not result in an evoked response (i.e., capture). In such instances, information pertaining to after potential or polarization artifact may be more readily acquired as myocardial response may be expected to be minimal. Accordingly, various exemplary methods, devices, systems, etc., described herein optionally include delivery of a stimulus during a refractory period of the myocardium and acquisition of information related to electrode potential.

Figure 3B:
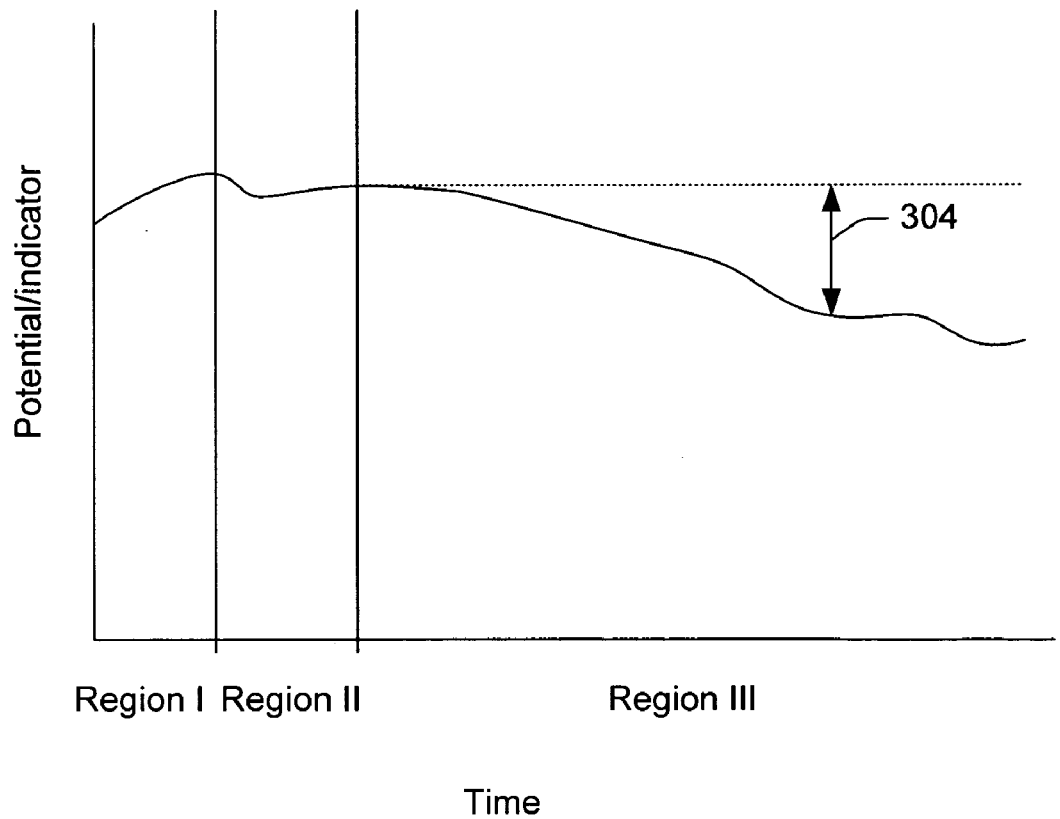
FIG. 3B is a plot of potential or an indicator thereof versus time.

FIG. 3B shows a plot 302 of a scenario where potential signal or an indicator thereof may vary over time. A first region, Region I, corresponds to an increase in stimulation threshold during the first several weeks following implantation, for example, due to development of a conductive but nonexcitable fibrotic capsule that may encase or surround at least part of an electrode. A second region, Region II, corresponds to several weeks thereafter wherein, for example, inflammation subsides. The capture threshold may subsequently decline, remain stable, or increase depending on factors such as chronic foreign body response at the electrode-tissue interface. A third region, Region III, corresponds to maturation of the electrode/body interface. However, in this region, the potential or indicator thereof may change due to various physiological factors, as represented by the deviation 304 from a selected baseline value. Such a change or deviation may be due to changes in evoked response and/or changes in electrode polarization or after potential. Such a change is optionally compensated, normalized, etc. to distinguish information relating to electrode potential or after potential from other potential information. As described herein, electrode polarization or after potential may change, for example, in such a region and be indicative of patient condition. Various exemplary methods, devices, systems, etc., described herein aim to track electrode polarization or after potential over time and optionally adjust patient therapy in response to such information.

Figure 4:
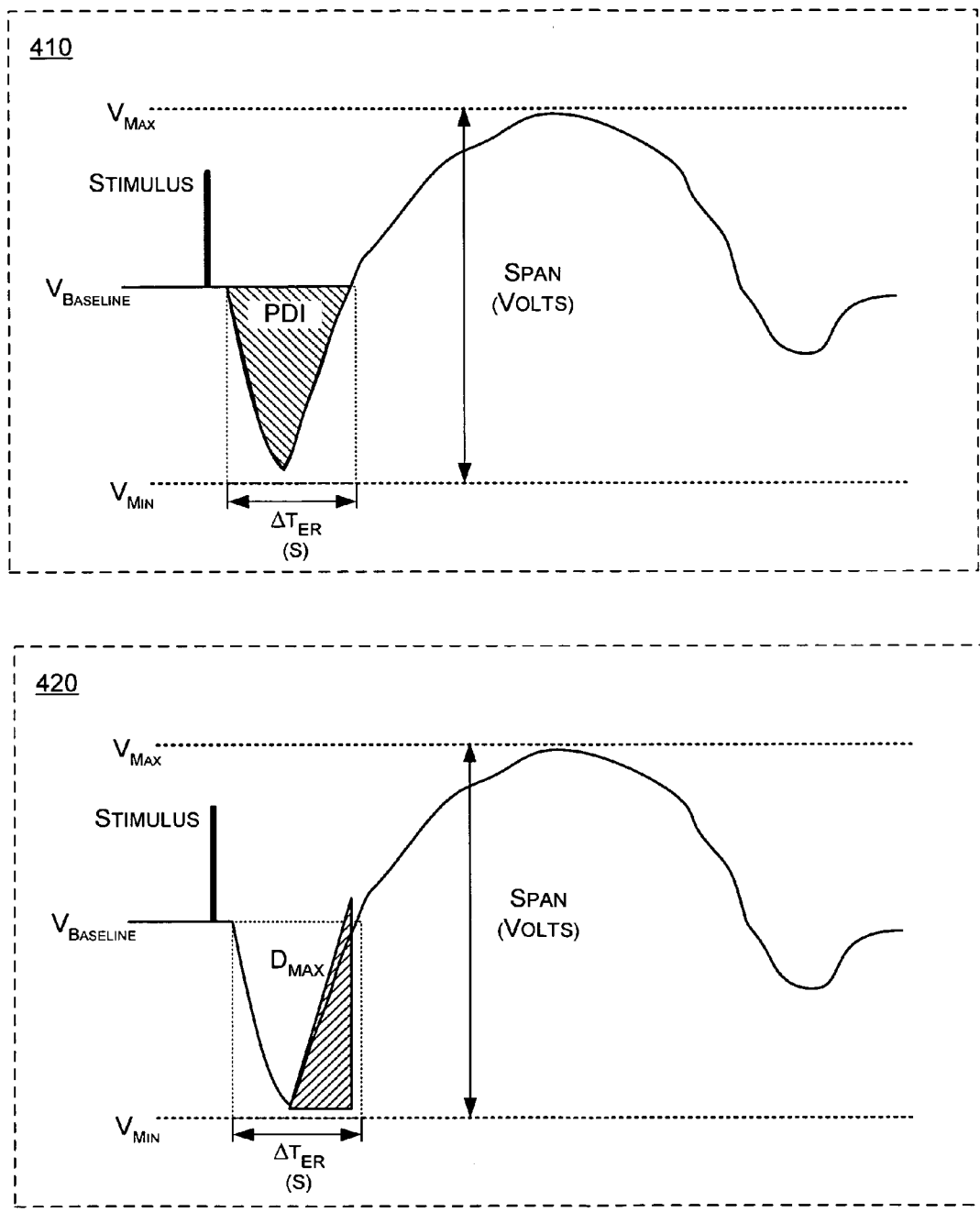
FIG. 4 is a series of plots for an integral analysis techniques and a derivative analysis technique related to intracardiac electrogram information.

Various techniques exist as to analysis of potential information versus time following delivery of a stimulus. FIG. 4 includes a plot of potential versus time to exhibit an integration analysis of an IEGM 410 and a plot of potential versus time to illustrate a derivative analysis of an IEGM 420. The potential signal in both instances corresponds to an evoked response, responsive to a cardiac stimulus. The potential signal also includes any after polarization, which is typically of much less magnitude than the evoked response signal. As shown in the plots 410, 420, both of the IEGMs decrease from a baseline to a minimum as a result of tissue depolarization.

Both of the IEGM plots 410, 420 include various parameters associated with data acquisition and/or data analysis. For example, a span in volts defined by a maximum voltage ($V_{Max}$) and a minimum voltage ($V_{Min}$) and duration of a sampling window or period in seconds ($\Delta t_S$). Data acquisition may also rely on an offset voltage ($V_{Offset}$). In general, data acquisition occurs after a delay or void window with duration in seconds ($\Delta t_V$). The void window may be due to any of a variety of actions that prevent a signal from being sampled or disregard sampled information (e.g., blanking, blocking, recharge, device refractory, etc.). For example, a device may include a void window or period to minimize interference from a stimulus or after polarization. In the latter instance, some devices may apply a counter potential to minimize after polarization prior to sampling of a signal (e.g., recharge). A device may use a device refractory window wherein sampled information is ignored, not analyzed, not stored, etc. In general, a sampling window may commence after all blanking, device refractory windows, etc.

A blanking or a blocking window may aim to ensure that ringing does not occur in a sense amplifier. This may be accomplished via software and/or hardware. For example, hardware blocking may include switching to electrically disconnect a lead conductor from a circuit during delivery of a cardiac stimulus and hardware blanking may include shorting a lead conductor or amplifier input during delivery of a cardiac stimulus while software blanking may ignore output of a sensing amplifier. A recharge window may immediately follow a pacing stimulus and include reversing current flow across the stimulus electrodes to reduce electrode polarization.

Referring again to the plot 410, integration analysis may include determining a depolarization integral (PDI). A PDI may be determined by summing acquired potential values for a given sampling window (e.g., $\Delta T_{ER}$). Typically, a sampling duration and a sampling period or frequency allow for determination of a PDI value in units of potential and time. While an integral is shown, other mathematical techniques may be applied to extract information from a depolarization signal. For example, derivative versus time, amplitude versus time, etc., may yield valuable information.

The plot 420 shows a derivative analysis wherein a maximum derivative of potential with respect to time ($D_{Max}$) occurs during a rise from the minimum potential to the baseline potential. In various human models, the maximum derivative typically occurs in range of about 12 ms to about 35 ms after the delivery of a cardiac stimulus. However, the maximum derivative may occur at an earlier time (see, e.g., the plot 300 of FIG. 3A).

Acquisition of data to determine the maximum derivative occurs during a sampling window, $\Delta T_{ER}$. In the plots 410, 420 the sampling window commences after a void duration that follows the stimulus (e.g., $\Delta T_{Void}$, not labeled). In some exemplary methods, devices, systems, etc., described herein the void duration may be reduced and the sampling window commenced earlier to allow for acquisition of more electrode polarization information.

Figure 5:
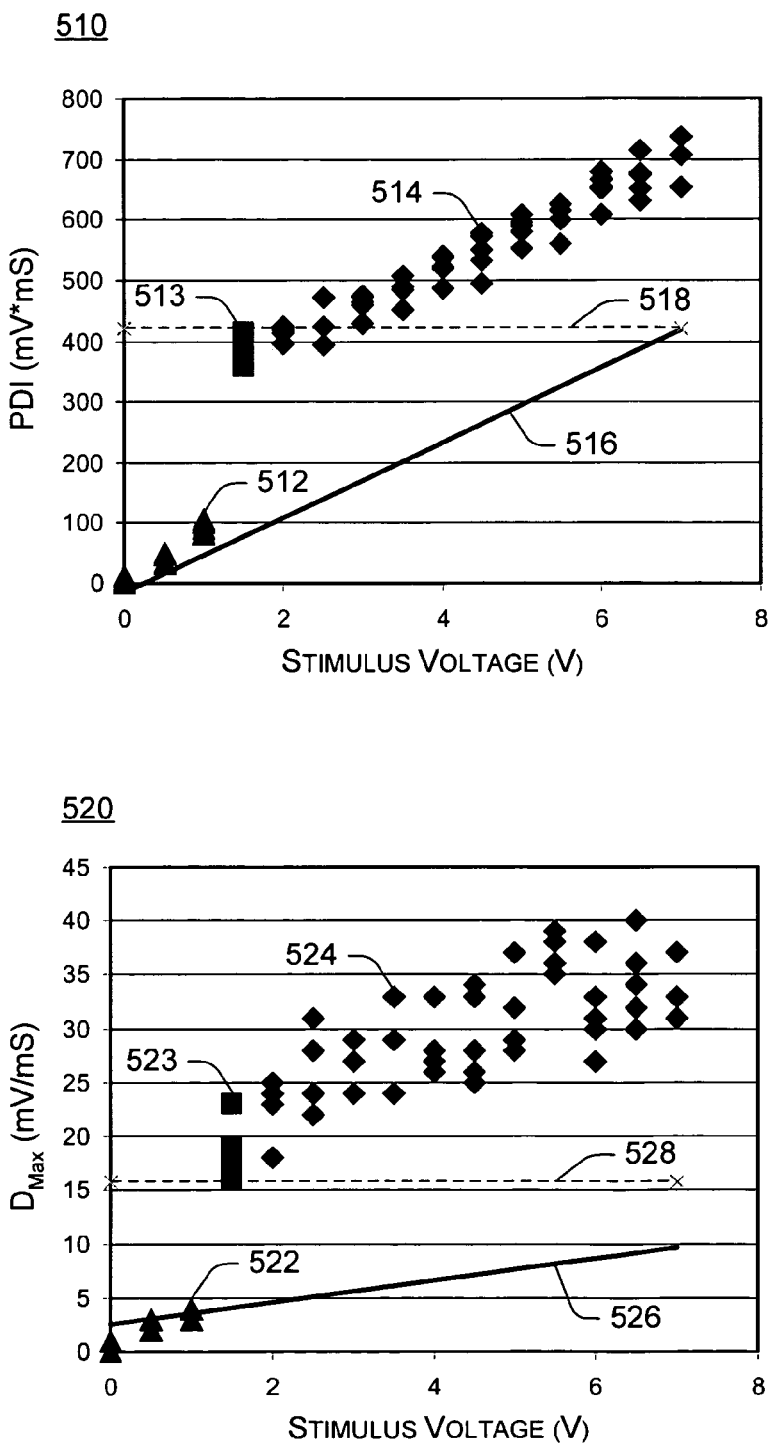
FIG. 5 is a series of plots for capture and non-capture events as analyzed using the integral technique and the derivative technique of FIG. 4.

FIG. 5 shows a plot of PDI data versus stimulus potential in volts 510 and a plot of $D_{Max}$ versus stimulus potential in volts 520. At low stimulus voltage, which corresponds to low stimulus energy, capture does not occur (see, e.g., data 512, 522). However, a trend appears wherein PDI and $D_{Max}$ increase with increasing stimulus voltage. The increase in PDI and $D_{Max}$ corresponds at least in part to increasing electrode polarization (e.g., after potential or polarization artifact) with increasing stimulus voltage. Based on such non-capture data (or myocardial refractory period data), a relationship may be established between electrode polarization and stimulus voltage. As shown in the exemplary plots 510, 520, the PDI and $D_{Max}$ values increase substantially linearly with respect to increasing stimulus voltage as represented by lines 516, 526, respectively.

At some stimulus voltage threshold level, capture occurs (513, 523). Horizontal lines 518, 528 approximate PDI and $D_{Max}$ values that correspond to capture. PDI data 514 and $D_{Max}$ data 524 at stimulus voltages above capture indicate that a relationship between electrode polarization and stimulus voltage remains even in the presence of capture. The exemplary data of the plots 510, 520 indicate that the relationship is approximately the same as for non-capture. Thus, the relationship between electrode polarization and stimulus voltage is somewhat independent of capture or non-capture conditions. Hence, the relationship between electrode polarization and stimulus voltage is substantially independent of an evoked response. Similarly, electrode polarization may be expected to have little dependence on other possible conditions such as fusion and pseudofusion; noting however that beat-to-beat fusion and pseudofusion can exhibit great irregularity in PDI and $D_{Max}$ values.

In the plots 510, 520, the threshold values 518, 528 may be used in an exemplary method, device, system, etc., to trigger therapy, adjustment of therapy, notification, etc. For example, if electrode polarization decreases, then the slope of the lines 516, 526 will decrease correspondingly, for capture events 514, 524, the contribution of electrode polarization to the PDI or $D_{Max}$ value will decrease. Thus, for a capture event, if a PDI or $D_{Max}$ value falls below the threshold PDI value 518 or the threshold $D_{Max}$ value 528, then a likely cause is decrease in electrode polarization.

Figure 6:
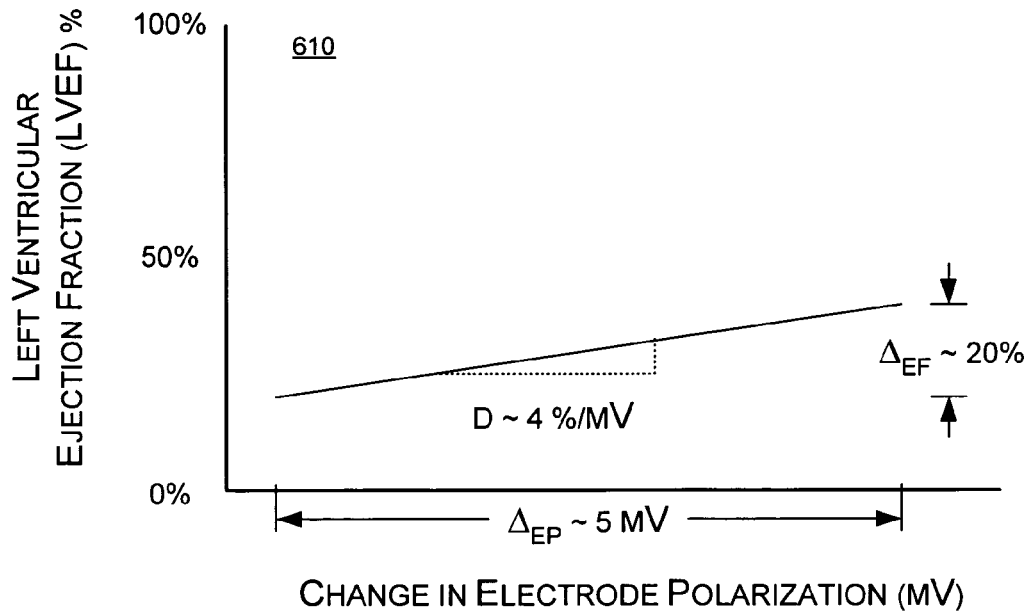
FIG. 6 is a series of plots that relate left ventricular ejection fraction to change in electrode polarization and to heart failure.
Figure 6:
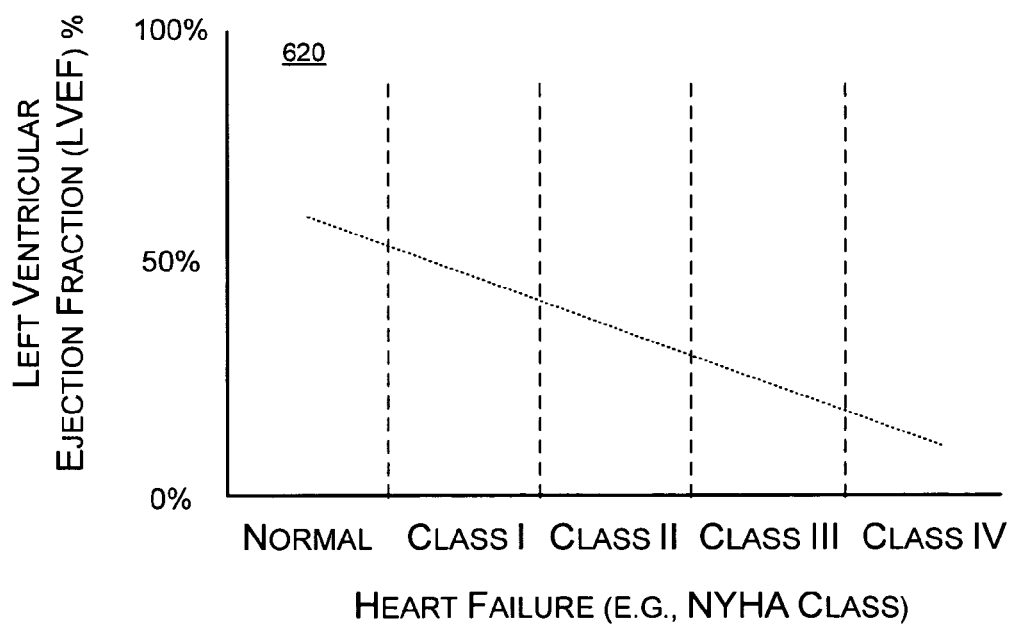

FIG. 6 shows a plot 610 of left ventricular ejection fraction (LVEF) in percent versus a change in electrode polarization in millivolts wherein the electrode polarization corresponds to a set stimulus voltage or wherein the electrode polarization has been corrected to account for changes in stimulus voltage. Importantly, the plot 610 indicates that a relationship exists between LVEF and change in electrode polarization or corrected electrode polarization. In the exemplary plot 610, the relationship is linear wherein a 1% change in LVEF corresponds to approximately a 0.25 mV increase in electrode polarization. Thus, as LVEF increases, electrode polarization may be expected to increase. Conversely, as LVEF decreases, electrode polarization may be expected to decrease. In general, LVEF is defined as the result of blood volume in the left ventricle at the end of diastolic minus blood volume in the left ventricle at the end of systolic divided by the blood volume in the left ventricle at the end of diastolic. Thus, as less blood is ejected from the heart (e.g., left ventricle), the ejection fraction decreases.

The plot 610 represents findings of a recent study by Freedman et al., "Correlation between Magnitude of Lead Polarization and Ejection Fraction in Pacemaker Patients," stated that "polarization signals were highly correlated with EF (r=0.2, p=0.005)" and that "an increase in EF of 1% predicted an increase in polarization of 0.25 mV". Further, Freedman et al. found that the correlation was independent of type of implanted lead. Yet further, Freedman et al. noted that polarization signals were lower in patients with higher NYHA class.

FIG. 6 also shows a plot 620 of LVEF versus heart failure, for example, according to NYHA class. A relationship between LVEF and heart failure typically exists where a decrease in LVEF corresponds to a progression or worsening of heart failure. A study by Moschovitis et al. "The Prevalence of Anemia in Chronic Heart Failure," *Int J Cardiol.* 202 November; 86(1):115-21, found an inverse relationship between NYHA class and LVEF with class I patients having an average ejection fraction of 45%, class II patients having an average LVEF of 32%, class III patients having an average LVEF of 25% and class IV patients having an average LVEF of 25%. In addition, Moschovitis et al. found of patients with anemia (15%, hemoglobin<120 g/l) more were in NYHA classes III and IV (19%) compared to classes I and II (8%, p<0.05). This study also noted that literature reports an incidence of anemia in about 56% of heart failure patients.

Other studies on anemia and/or hemodilution indicate a relationship with heart failure. A study by Ezekowitz et al., "Anemia Is Common in Heart Failure and Is Associated With Poor Outcomes," *Circulation.* 2003:107: 223-225, states several possible explanations for their findings, including reduced hemoglobin as a marker for "the epiphenomena of advanced heart failure (such as hemodilution due to volume overload, malnutrition from cardiac cachexia, or renal insufficiency)" and that "heart failure may cause anemia of chronic disease through cytokine-mediated bone marrow suppression." Ezekowitz et al. suggest treatment of anemia through use of erythropoietin and intravenous iron.

A study by Androne et al., "Hemodilution Is Common in Patients With Advanced Heart Failure," *Circulation.* 2003; 107: 226-229, states that "patients with hemodilution tend to do worse than patients with true anemia, which suggest that volume overload may be an important mechanism contributing to the poor outcome in anemic CHF patients." While Androne et al. reported LVEF values of 22+/−6% for hemodilution patients and 27+/−7% for true anemia patients, they also stated that LVEF values did not differ between the two groups (e.g., p not less than 0.05). However, pulmonary capillary wedge was significantly higher in the hemodilution group (p<0.01). The study of Androne et al. also refers to yet other studies that established relationships between anemic condition and NYHA class (e.g., 9% in NYHA class I and 79% in NYHA class IV).

Thus, while the plot 620 shows a relationship between LVEF and NYHA class, a similar relationship may be expected between anemia and NYHA class; hence, change in electrode polarization may indicate a change in heart failure or more particularly LVEF, NYHA class and/or anemic condition.

In various examples, while PDI and $D_{Max}$ are mentioned, other IEGM analyses may be used as indicators of polarization (e.g., amplitude, amplitude as a derivative of voltage, etc.). In general, an IEGM may be analyzed for polarization information (e.g., one or more values indicative of electrode polarization) and such information may be used to determine cardiac condition or therapy.

Figure 7:
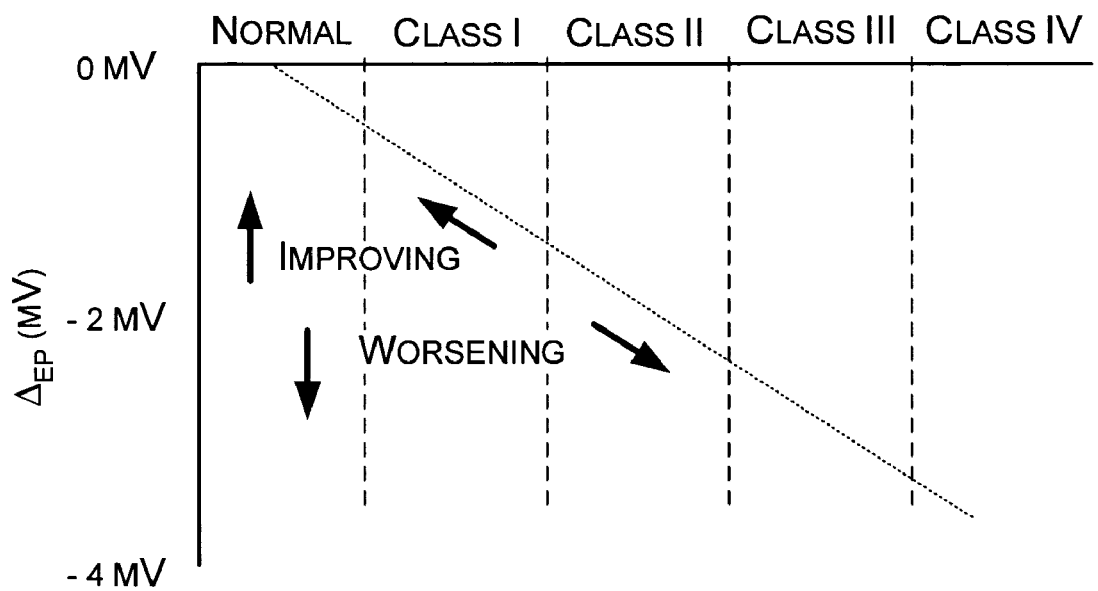
FIG. 7 is a plot of change in electrode polarization versus heart failure.

FIG. 7 shows a plot 700 of change in electrode polarization in mV versus heart failure as NYHA class. As discussed above, a decrease in electrode polarization (e.g., for a set stimulus voltage or corrected for stimulus voltage) corresponds to worsening heart failure. Conversely, an increase in electrode polarization (e.g., for a set stimulus voltage or corrected for stimulus voltage) corresponds to improving condition. As mentioned above, change in electrode polarization may indicate a change in heart failure or more particularly LVEF, NYHA class and/or anemic condition; thus, the abscissa of the plot 700 may be replaced by LVEF and/or anemic condition. Other parameters may be related to change in electrode potential based on theoretical and/or experimental data.

Various exemplary methods, devices, systems, etc., optionally use other information in conjunction with potential information. For example, as mentioned with respect to the device 100 of FIGS. 1 and 2, impedance information may be used in conjunction with electrode potential information. Analysis of impedance information and electrode potential information may increase accuracy of a diagnosis or allow for selection of a more appropriate cardiac therapy. In particular, polarization information and impedance information may be acquired substantially simultaneously for a cardiac cycle. These two measures may be compared on a beat-by-beat or other basis to more accurately determine cardiac condition or therapy.

Various exemplary methods, devices, systems, etc., may use pressure information in conjunction with polarization information. For example, left atrial pressure has been shown to be measurable via a microsensor and indicative of cardiac condition (e.g., cardiac output, etc.). Analysis of pressure information and electrode potential information may increase accuracy of a diagnosis or allow for selection of a more appropriate cardiac therapy. Other examples may use other pressure information (e.g., ventricular pressure, right atrial pressure, other pressure). Various examples may use more than two measures in addition to electrode potential to determine cardiac condition or therapy. In general, where potential information is mentioned, other information may optionally be used in conjunction with the potential information.

Some pacing systems use algorithms that aim to automatically adjust output and/or assess capture threshold, usually on a periodic basis. Some of these systems are capable of measuring and/or determining electrode polarization. A particular system uses the AUTOCAPTURE™ algorithm (St. Jude Medical, Cardiac Rhythm Management Division, Sylmar, Calif.) to automatically adjust output and/or assess capture threshold.

The AUTOCAPTURE™ algorithm runs a capture threshold assessment test once every eight hours. To perform this test, the paced and sensed AV delays are temporarily shortened to about 50 ms and to about 25 ms, respectively. The AUTOCAPTURE™ algorithm generally uses a bottom-up approach (also referred to as an "up threshold") and a back-up pulse for safety when an output pulse does not result in capture. With respect to use of a back-up pulse, an output pulse of about 4.5 volts is typically sufficient to achieve capture.

In clinical follow-up, a care provider may perform a threshold test to determine if the algorithm for capture is working properly and for further assessment. In systems that use the AUTOCAPUTRE™ algorithm, a follow-up clinical test includes automatically and temporarily setting PV delay and AV delay times to about 25 ms and about 50 ms, respectively, which acts to minimize risk of fusion. Fusion may compromise measurement of an ER signal, especially ER signal amplitude. If results from the follow-up test indicate that enabling of the algorithm would not be safe due to too low an evoked response or too high of an electrode polarization signal, then the algorithm may be disabled and a particular, constant output programmed to achieve suitable capture. In this aforementioned example, sensitivity may be set as it relates to detection of an ER signal.

The follow-up tests typically work top down. If loss of capture occurs, a first output adjustment step typically sets a high output and then decreases output by about 0.25 volts until loss of capture occurs (also referred to as a "down threshold"). At this point, output is increased by a lesser amount (e.g., about 0.125 volts) until capture occurs. Once capture occurs, a working or functional margin of about 0.25 volts is added to the capture threshold output value. Hence, the final output value used is the capture threshold plus a working margin. Systems that use a fixed output use a safety margin ratio instead of an absolute added amount. The safety margin is a multiple of the measured capture threshold, commonly 2:1 or 100% to allow for fluctuations in the capture threshold between detailed evaluations at the time of office visits.

With respect to a down threshold approach, in instances where loss of capture occurs, a first output adjustment step typically increases output until capture is restored. Steps used in the AUTOCAPTURE™ algorithm are typically finer than those used in a routine follow-up capture threshold test. At times, a down threshold algorithm may result in a threshold that varies as much as 1 volt from the result of an up threshold algorithm. This has been termed a Wedensky effect. In general, an actual output setting (e.g., including safety margin) may be adjusted to account for whether a patient is pacemaker dependent. In a patient who is not dependent on the pacing system, a narrower safety margin may be selected than would be the case for a patient whom the physician considers to be pacemaker dependent.

As described above, whether an up-threshold or down-threshold test is used, non-capture occurs in during determination of an appropriate stimulus output voltage. An IEGM acquired during non-capture allows for determination of electrode polarization. Thus, capture threshold algorithms such as the AUTOCAPTURE™ algorithm are suitable for acquiring electrode polarization information. Further, stimulus voltage may be noted for a non-capture event together with integral, derivative and/or other information relating to electrode polarization. Yet further, sampling window, void window, etc., may be set to acquire earlier electrode polarization information.

Figure 8:
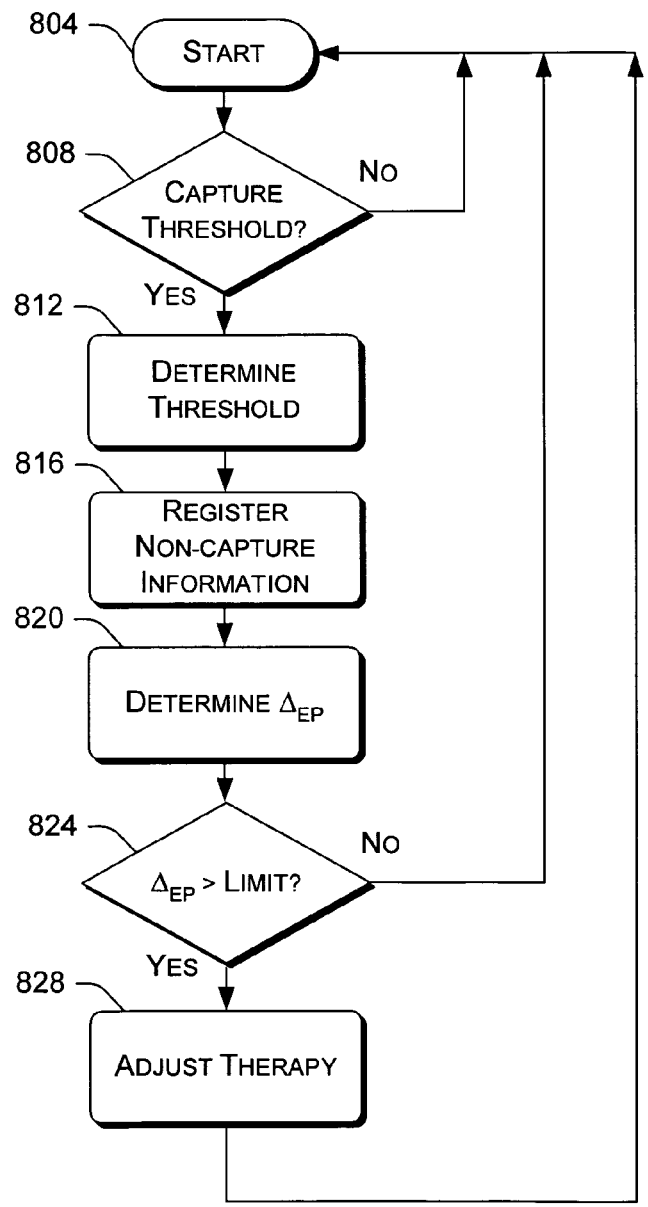
FIG. 8 is a block diagram of an exemplary method for determining change in electrode polarization based at least in part on non-capture events and optionally adjusting therapy in response to such a change, as appropriate.

FIG. 8 shows an exemplary method 800 for acquiring electrode polarization information and optionally adjusting therapy in response thereto. The method 800 commences in a start block 804 wherein an implantable cardiac therapy device delivers cardiac stimuli and/or acquires information related to cardiac performance. A decision block 808 follows to decide whether a capture threshold assessment should occur. As already mentioned, conventional devices may perform such assessments according to a schedule and/or user input (e.g., by a care provider). In some instances, a capture threshold assessment may occur in response to an event such as loss of capture event and/or sensed information. If the decision block 808 does not indicate a need for a threshold assessment, then the method 800 may continue at the start block 804; however, if the block 808 decides a need for an assessment exists, then the method 800 continues in a determination block 812 for determining an appropriate threshold.

As already mentioned, a threshold determination typically includes delivery of at least one stimulus followed by a non-capture event. According to the exemplary method 800, a register block 816 registers or records information related to one or more non-capture events, in particular, information pertaining to electrode polarization. Another determination block 820 follows that determines a $\Delta_{EP}$ value based at least in part on the registered information. The $\Delta_{EP}$ value determination may rely on previously acquired information pertaining to one or more stimulus voltage and corresponding electrode polarizations. For example, at a first time, an exemplary method may include acquiring information related to electrode polarization for one or more stimulus voltages or energies. At a second time, additional electrode polarization information may be acquired for a given stimulus voltage. Use of the information acquired at the first time and the information acquired at the second time may then allow for determination of a change in electrode polarization corresponding to the duration between the first and second times. In this example, a single value (e.g., integral, derivative, amplitude, etc.) acquired at the first time may in some instances be sufficient to determine further action. Consider a value of 1 determined for a stimulus voltage of 1 volt at a first time and then a value less than 1 determined for a stimulus voltage of 1 volt or more at a second time; in this instance electrode polarization has decreased and it is likely that the patient's condition has worsened. In this example, the values may be normalized and/or otherwise compensated to account for other factors (e.g., evoked response changes, interface changes, etc.).

Another decision block 824 follows the determination block 820 wherein the $\Delta_{EP}$ value is compared to a limit. If the $\Delta_{EP}$ value compares favorably (e.g., less than the limit), then either the electrode polarization has not changed, increased or decreased in a manner that does not warrant any further action. In this instance, the method 800 returns to the start block 804. If the $\Delta_{EP}$ value compares unfavorably (e.g., exceeds the limit), then the method 800 continues in an adjustment block 828 that adjusts therapy to account, for example, a worsening in patient condition. While the exemplary method 800 uses electrode polarization information, other information may be used in conjunction with electrode polarization information (e.g., pressure, impedance, etc.).

Figure 9:
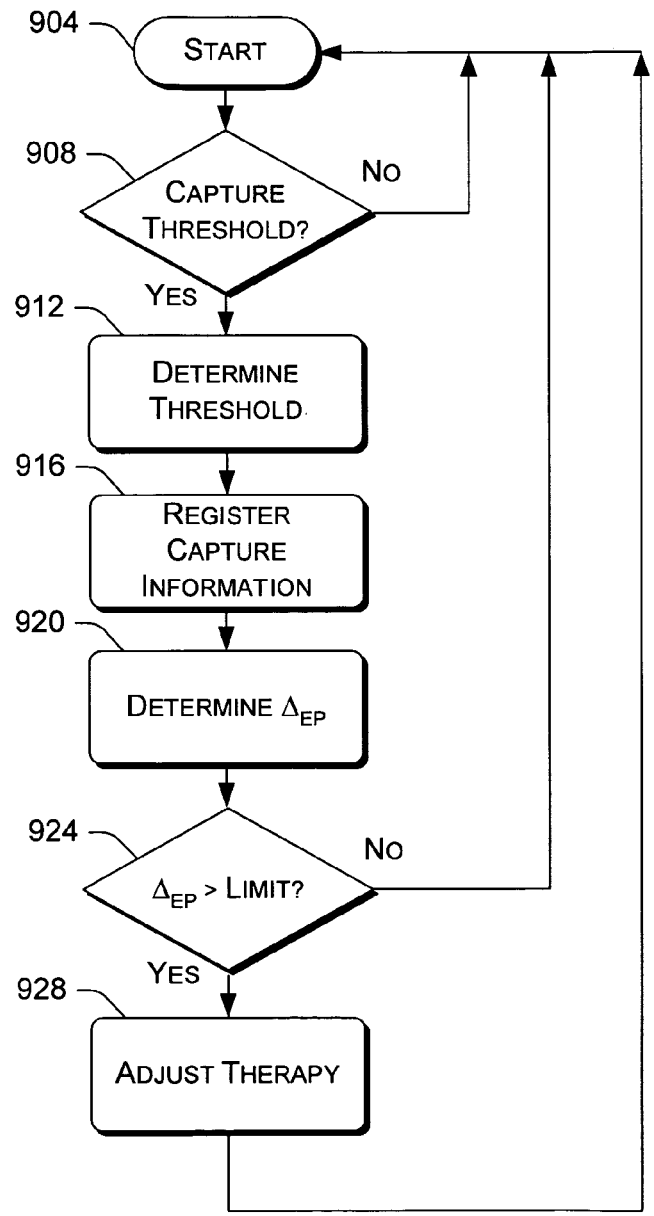
FIG. 9 is a block diagram of an exemplary method for determining change in electrode polarization based at least in part on capture events and optionally adjusting therapy in response to such a change, as appropriate

FIG. 9 shows an exemplary method 900 for acquiring electrode polarization information and optionally adjusting therapy in response thereto. The method 900 commences in a start block 904 wherein an implantable cardiac therapy device delivers cardiac stimuli and/or acquires information related to cardiac performance. A decision block 908 follows to decide whether a capture threshold assessment should occur. As already mentioned, conventional devices may perform such assessments according to a schedule and/or user input (e.g., by a care provider). In some instances, a capture threshold assessment may occur in response to an event such as loss of capture event and/or sensed information. If the decision block 908 does not indicate a need for a threshold assessment, then the method 900 may continue at the start block 904; however, if the block 908 decides a need for an assessment exists, then the method 900 continues in a determination block 912 for determining an appropriate threshold.

As already mentioned, a threshold determination typically includes delivery of stimuli at more than one stimulus voltage or energy wherein one or more of the stimuli capture and wherein one or more of the stimuli do not capture. According to the exemplary method 900, a register block 916 registers or records information related to one or more capture events, in particular, information pertaining to electrode polarization. While the exemplary method 800 pertains to electrode polarization based on non-capture events and the exemplary method 900 pertains to electrode polarization based on capture events, other exemplary methods may use a combination of capture and non-capture events as appropriate. Noting that capture event information will typically include evoked response information (e.g., depolarization and/or repolarization) and electrode polarization information whereas non-capture event information will typically include electrode polarization information and perhaps some minimal localized depolarization and/or repolarization information.

Referring again to the method 900, another determination block 920 follows the register block 916 that determines a $\Delta_{EP}$ value based at least in part on the registered information. The $\Delta_{EP}$ value determination may rely on previously acquired information pertaining to one or more stimulus voltage and corresponding electrode polarizations. For example, at a first time, an exemplary method may include acquiring information related to electrode polarization for one or more stimulus voltages or energies. At a second time, additional information that includes electrode polarization information may be acquired for a given stimulus voltage. Use of the information acquired at the first time and the information acquired at the second time may then allow for determination of a change in electrode polarization corresponding to the duration between the first and second times. In this example, a single value (e.g., integral, derivative, amplitude, etc.) acquired at the first time may in some instances be sufficient to determine further action. Consider a value of 1 determined for a stimulus voltage of 1 volt at a first time and then a value less than 1 determined for a stimulus voltage of 1 volt or more at a second time; in this instance electrode polarization has decreased and it is likely that the patient's condition has worsened. In this example, the values may be normalized and/or otherwise compensated to account for other factors (e.g., evoked response changes, interface changes, etc.). Referring to the plots 510, 520 of FIG. 5, a PDI or $D_{Max}$ threshold value may be used in a comparison or decision block. In other examples, an amplitude value or other value may be used.

Another decision block 924 follows the determination block 920 wherein the $\Delta_{EP}$ value is compared to a limit. If the $\Delta_{EP}$ value compares favorably (e.g., less than the limit), then either the electrode polarization has not changed, increased or decreased in a manner that does not warrant any further action. In this instance, the method 900 returns to the start block 904. If the $\Delta_{EP}$ value compares unfavorably (e.g., exceeds the limit), then the method 900 continues in an adjustment block 928 that adjusts therapy to account for, for example, a worsening in patient condition. While the exemplary method 900 uses electrode polarization information, other information may be used in conjunction with electrode polarization information (e.g., pressure, impedance, etc.).

While the exemplary methods 800, 900 generally pertain to ventricular threshold assessments, various exemplary methods may pertain to atrial threshold assessments. While the exemplary method 800, 900 refer generally to capture thresholds, other techniques may be used to acquire electrode polarization information. For example, sensitivity algorithms may be used to acquire electrode polarization information.

Various exemplary methods, devices, systems, etc., include use of potential information following delivery of a stimulus wherein one or more characteristics of the potential information are used to detect a change in electrode polarization or after potential. For example, consider calculating a difference of PDI–ER(V2) (PDI of an evoked response at voltage V2) and PDI–ER(V1) (PDI of an evoked response at voltage V1) wherein the difference is representative of electrode polarization or after potential and then comparing this value to a limit or other value for a different time. Such a difference may be divided by a difference in voltage (i.e. V2–V, V1–V2) and then compared to a limit or other value. Based on such comparisons, a decision may be made with respect to therapy and/or a determination made as to patient condition (e.g., HF, hemodilution, EF, anemia, etc.).

In some instances, a patient motion and/or position sensor may be used to acquire information to determine patient activity, position, etc. An exemplary method, device, system, etc., may acquire electrode polarization information in response to patient motion and/or position information. For example, an algorithm to acquire electrode polarization information may be triggered approximately 15 to 20 minutes after a patient reclines or reduces motion below a certain level. In another example, potential information may be compensated and/or otherwise adjusted based on patient position (e.g., posture). Some studies (e.g., Schuchert, *PACE*, Vol. 22, October 1999) indicate that and ER component of a potential signal may depend on posture whereas electrode polarization or after potential may not. Again, such distinctions may aid in analysis or determination of electrode polarization or after potential.

As described herein, various exemplary techniques allow for polarization measurements. Such techniques may monitor and store polarization measurements on a regular basis. Polarization values as a function of time may be used in conjunction with other measures. For example, polarization values may be used in conjunction with evoked response morphology or other evoked response parameters and compared or otherwise analyzed with respect to time. Such values are optionally related to changes in ejection fraction or other cardiac function where a change in a value or values could be used to indicate a change in cardiac function. This example may serve as a basis for a closed-loop controller to adjust an implantable cardiac therapy device.

In the case for patients without any significant correlation between polarization and cardiac condition, the polarization values may be used for setting capture thresholds.

In various examples, polarization measurements are made while a patient is at rest (e.g., based on sensors like an accelerometer). A delay may occur after the patient is at rest and then measurements made thereafter (e.g. 15 minutes, etc.). Various exemplary methods, devices, systems, etc., optionally note adverse changes, verify changes and/or communicate an alarm.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method of operating an implantable cardiac stimulation device comprising:

determining a first slope of maximum derivative values of cardiac electrical activity ($D_{Max}$) versus stimulus potential at a first time as a first value indicative of electrode polarization;

determining a second slope of $D_{Max}$ versus stimulus potential at a second time as a second value indicative of electrode polarization;

using the first slope and the second slope to determine a change in electrode polarization corresponding to the duration between the first and second times by comparing the first slope of $D_{Max}$ versus stimulus potential to the second slope of $D_{Max}$ versus stimulus potential as a surrogate of heart condition to determine whether a change in cardiac condition has occurred; and adjusting a cardiac stimulation therapy delivered to a patient by the implantable cardiac stimulation device.

2. The method of claim 1 wherein the stimulus potential arises from delivering cardiac pacing therapy.

3. The method of claim 2 wherein the delivering delivers the cardiac pacing therapy to a ventricle.

4. The method of claim 2 wherein the delivering delivers the cardiac pacing therapy to an atrium.

5. A method of operating an implantable cardiac stimulation device comprising:

determining a first slope of depolarization integral (PDI) data versus stimulus potential at a first time as a first value indicative of electrode polarization;

determining a second slope of PDI data versus stimulus potential at a second time as a second value indicative of electrode polarization;

using the first slope and the second slope to determine a change in electrode polarization corresponding to the duration between the first and second times by comparing the first slope of PDI data versus stimulus potential to the second slope of PDI data versus stimulus potential as a surrogate of heart condition to determine whether a change in cardiac condition has occurred; and adjusting a cardiac stimulation therapy delivered to a patient by the implantable cardiac stimulation device.

6. The method of claim 5 wherein the stimulus potential arises from delivering cardiac pacing therapy.

7. The method of claim 6 wherein the delivering delivers the cardiac pacing therapy to a ventricle.

8. The method of claim 6 wherein the delivering delivers the cardiac pacing therapy to an atrium.

\* \* \* \* \*

UNITED STATES PATENT AND TRADEMARK OFFICE
CERTIFICATE OF CORRECTION

PATENT NO.       : 7,627,366 B1                                           Page 1 of 1
APPLICATION NO. : 11/123300
DATED            : December 1, 2009
INVENTOR(S)      : Karicherla et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this

Second Day of November, 2010

David J. Kappos
*Director of the United States Patent and Trademark Office*